(12) United States Patent
Li et al.

(10) Patent No.: US 11,396,646 B2
(45) Date of Patent: Jul. 26, 2022

(54) STEVIOL GLYCOSYLTRANSFERASES AND GENES ENCODING THE SAME

(71) Applicant: QTG Development, Inc., Chicago, IL (US)

(72) Inventors: Xu Li, Cary, NC (US); Han-Yi Chen, Concord, NC (US); Nickolas Anderson, Arden Hills, MN (US); Amanda Waters, Champlin, MN (US)

(73) Assignee: QTG Development, Inc.

( * ) Notice: Subject to any disclaimer, the term of this patent is extended or adjusted under 35 U.S.C. 154(b) by 0 days.

(21) Appl. No.: 16/887,435

(22) Filed: May 29, 2020

(65) Prior Publication Data

US 2021/0371831 A1 Dec. 2, 2021

(51) Int. Cl.
*C12P 15/00* (2006.01)
*C12P 19/56* (2006.01)
*C12N 15/82* (2006.01)
*C12N 9/10* (2006.01)

(52) U.S. Cl.
CPC ............ *C12N 9/1048* (2013.01); *C12P 19/56* (2013.01); *C12Y 204/00* (2013.01)

(58) Field of Classification Search
CPC ........... C12P 15/00; C12P 19/44; C12P 5/007; C12P 19/12; A23L 27/36; A23L 2/60; C12N 9/1051; C12N 9/1048; C12N 15/70; C12N 15/74; C12N 15/8201; C12Y 204/01; C12Y 204/00
USPC ....... 435/78, 127, 254.11, 252.3, 320.1, 193, 435/195; 536/23.2
See application file for complete search history.

(56) References Cited

FOREIGN PATENT DOCUMENTS

WO 2017/198681 11/2017

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
International Search Report and Written Opinion dated Nov. 26, 2021, in PCT/US2021/034738.
Kim et al., "Overexpression of SrUGT76G1 in Stevia alters major steviol glycosides composition towards improved quality," Plant Biotechnology Journal, vol. 17, No. 6, Dec. 19, 2018, pp. 1037-1047.
Database UniProt [Online], RecName: Full=Glycosyltransferase, retrieved from EBI accession No. UNIPROT: A0A5N6N2A3, Apr. 22, 2020.
Wang et al., "Structure, mechanism and engineering of plant natural product glycosyltransferases," FEBS Letters, Elsevier, Amsterdam, NL, vol. 583, No. 20, Oct. 20, 2009, pp. 3303-3309.

* cited by examiner

*Primary Examiner* — Robert B Mondesi
*Assistant Examiner* — Mohammad Y Meah
(74) *Attorney, Agent, or Firm* — Barnes & Thornburg LLP; Aisha R. Hasan

(57) ABSTRACT

Polynucleotides encoding corresponding polypeptides capable of glycosylating steviol at its C-19 position to produce a steviol glycoside, an expression vector including such a polynucleotide, a method for producing a steviol glycoside by culturing a recombinant host cell containing such an expression vector under conditions in which the cell expresses the UDP-glycosyltransferase from the polynucleotide, and a method for producing a steviol glycoside by contacting a composition including steviol with a recombinant UDP-glycosyltransferase. The steviol glycoside can be steviol-19-O-glycoside. The recombinant host cell containing such an expression vector can be a bacterial cell, a plant cell, or a fungal cell, an animal cell, or a multicellular organism such as a plant.

20 Claims, 2 Drawing Sheets

Specification includes a Sequence Listing.

SEQUENCE LISTING

<160> NUMBER OF SEQ ID NOS: 4

<210> SEQ ID NO 1
<211> LENGTH: 1479
<212> TYPE: DNA
<213> ORGANISM: Stevia rebaudiana
<220> FEATURE:
<221> NAME/KEY: exon
<222> LOCATION: (1)..(1479)

<400> SEQUENCE: 1

```
atg gcc acc aac aaa gtc cat ttc ctt cta att ccc cac ata ggc ccc      48
Met Ala Thr Asn Lys Val His Phe Leu Leu Ile Pro His Ile Gly Pro
1               5                   10                  15 ggt cac acg atc ccc atg atc gac atg gct aaa ctg ctc gct aaa caa      96
Gly His Thr Ile Pro Met Ile Asp Met Ala Lys Leu Leu Ala Lys Gln
                20                  25                  30 cca aac gtt acg gtc acc atc gcc gtc aca ccg ctc aac gcc gcc cgt     144
Pro Asn Val Thr Val Thr Ile Ala Val Thr Pro Leu Asn Ala Ala Arg
            35                  40                  45 tac ggt ggc acc ctc gcc gga gcc atc acc gcc gga ctt ccg gtc cgg     192
Tyr Gly Gly Thr Leu Ala Gly Ala Ile Thr Ala Gly Leu Pro Val Arg
        50                  55                  60 ttt ttt gag ctc cca ttt ccg gca gta gag gct gga ttg cct gaa ggg     240
Phe Phe Glu Leu Pro Phe Pro Ala Val Glu Ala Gly Leu Pro Glu Gly
65                  70                  75                  80 tgt gaa agc aca gat caa atc cca agt gtg gtt tta atc cca aat ttt     288
Cys Glu Ser Thr Asp Gln Ile Pro Ser Val Val Leu Ile Pro Asn Phe
                85                  90                  95 tta tcc gcc att gat atg tta cag caa aag ctt gaa gaa cgg ttt gaa     336
Leu Ser Ala Ile Asp Met Leu Gln Gln Lys Leu Glu Glu Arg Phe Glu
            100                 105                 110 atg ata aac cct cgt ccg aat tgc atc ata tct gat aaa tac atg tca     384
Met Ile Asn Pro Arg Pro Asn Cys Ile Ile Ser Asp Lys Tyr Met Ser
        115                 120                 125 tgg acg ggt gat ttt gcg gat aag tat cgg tta ccg aga atc atg ttt     432
Trp Thr Gly Asp Phe Ala Asp Lys Tyr Arg Leu Pro Arg Ile Met Phe
    130                 135                 140 gat gga atg agt tgt ttt aac gag tta tgt tgt aat aat ttg tat gaa     480
Asp Gly Met Ser Cys Phe Asn Glu Leu Cys Cys Asn Asn Leu Tyr Glu
145                 150                 155                 160
```

```
cac aag gtg ttc gac ggt ttg cct gac tca gaa cca ttt gtt gtc ctg        528
His Lys Val Phe Asp Gly Leu Pro Asp Ser Glu Pro Phe Val Val Leu
            165                 170                 175 ggt tta cct gat cgg gtt gag ttg acc aga aac cag ctc cca ccg gag        576
Gly Leu Pro Asp Arg Val Glu Leu Thr Arg Asn Gln Leu Pro Pro Glu
            180                 185                 190 ttt aac ccg agc tcg gtt gac acg agt gca ttt cgc caa cgc gct aga        624
Phe Asn Pro Ser Ser Val Asp Thr Ser Ala Phe Arg Gln Arg Ala Arg
            195                 200                 205 gat gct gaa gtt agg gct tat ggg gtg gtg att aat agt ttt gat gaa        672
Asp Ala Glu Val Arg Ala Tyr Gly Val Val Ile Asn Ser Phe Asp Glu
    210                 215                 220 ctt gaa caa gaa tat gtt aat gag tat aag aaa tta aga ggg ggt aaa        720
Leu Glu Gln Glu Tyr Val Asn Glu Tyr Lys Lys Leu Arg Gly Gly Lys
225                 230                 235                 240 gtt tgg tgt atc gga cca ttg tcg cta tgc gat agc gac gat tcg att        768
Val Trp Cys Ile Gly Pro Leu Ser Leu Cys Asp Ser Asp Asp Ser Ile
                245                 250                 255 aaa tct caa agg gga aat gta gcc tca att aac gaa caa caa tgc cta        816
Lys Ser Gln Arg Gly Asn Val Ala Ser Ile Asn Glu Gln Gln Cys Leu
            260                 265                 270 aag tgg ctt gat tct cac gaa cca gag tca gta gta tac gcg tgt ttt        864
Lys Trp Leu Asp Ser His Glu Pro Glu Ser Val Val Tyr Ala Cys Phe
            275                 280                 285 ggt agt ttg gtt agg atc aat acg cct caa ctt att gag ctc ggt tta        912
Gly Ser Leu Val Arg Ile Asn Thr Pro Gln Leu Ile Glu Leu Gly Leu
            290                 295                 300 ggc cta gaa gca tca aat cgc ccg ttc att tgg gtg att aaa tcg gtt        960
Gly Leu Glu Ala Ser Asn Arg Pro Phe Ile Trp Val Ile Lys Ser Val
305                 310                 315                 320 cat aga gaa aag gaa gtt gag gaa tgg tta gcc gaa agc ggg ttt gag       1008
His Arg Glu Lys Glu Val Glu Glu Trp Leu Ala Glu Ser Gly Phe Glu
                325                 330                 335 gag agg gtt aaa cat aga ggt ttg ata ata cgc ggt tgg gcc cca caa       1056
Glu Arg Val Lys His Arg Gly Leu Ile Ile Arg Gly Trp Ala Pro Gln
            340                 345                 350 gtg cta atc ttg tcc cac ccg tca gtt gga ggg ttc tta aca cat tgt       1104
Val Leu Ile Leu Ser His Pro Ser Val Gly Gly Phe Leu Thr His Cys
            355                 360                 365 ggt tgg aac tcg act cta gaa tca gtg tct gct ggt gtt ccc atg atc       1152
Gly Trp Asn Ser Thr Leu Glu Ser Val Ser Ala Gly Val Pro Met Ile
            370                 375                 380 aca tgg cca cag ttc gca gag cag ttt att aac gag aag ctt gtg gtg       1200
Thr Trp Pro Gln Phe Ala Glu Gln Phe Ile Asn Glu Lys Leu Val Val
385                 390                 395                 400 caa gtt ttg ggg atc ggt gtc ggt gtt gga gct gat tcg gtt gtt cat       1248
Gln Val Leu Gly Ile Gly Val Gly Val Gly Ala Asp Ser Val Val His
                405                 410                 415 gtg ggt gaa gaa gat cgg ttt ggg gtg aaa gtt aag agt gag agc gtg       1296
Val Gly Glu Glu Asp Arg Phe Gly Val Lys Val Lys Ser Glu Ser Val
            420                 425                 430 aag aag gct atc gag cag gtg atg gat ggc ggg att gaa gga aat gag       1344
Lys Lys Ala Ile Glu Gln Val Met Asp Gly Gly Ile Glu Gly Asn Glu
            435                 440                 445 aga cga aag agc gtt aaa aaa ctc gcg ata att gcg aat aac gcg ata       1392
Arg Arg Lys Ser Val Lys Lys Leu Ala Ile Ile Ala Asn Asn Ala Ile
    450                 455                 460 aag gag ggt gga tct tct cat ttg aac ttg acc cta cta att caa gac       1440
Lys Glu Gly Gly Ser Ser His Leu Asn Leu Thr Leu Leu Ile Gln Asp
465                 470                 475                 480
```

```
ata atg cat cat tcg gat act tca tgt aaa gag tct tga                 1479
Ile Met His His Ser Asp Thr Ser Cys Lys Glu Ser
                485                 490
```

<210> SEQ ID NO 2
<211> LENGTH: 492
<212> TYPE: PRT
<213> ORGANISM: Stevia rebaudiana
<220> FEATURE:
<221> NAME/KEY: PEPTIDE
<222> LOCATION: (1)..(492)

<400> SEQUENCE: 2

Met Ala Thr Asn Lys Val His Phe Leu Leu Ile Pro His Ile Gly Pro
1               5                   10                  15

Gly His Thr Ile Pro Met Ile Asp Met Ala Lys Leu Leu Ala Lys Gln
            20                  25                  30

Pro Asn Val Thr Val Thr Ile Ala Val Thr Pro Leu Asn Ala Ala Arg
        35                  40                  45

Tyr Gly Gly Thr Leu Ala Gly Ala Ile Thr Ala Gly Leu Pro Val Arg
    50                  55                  60

Phe Phe Glu Leu Pro Phe Pro Ala Val Glu Ala Gly Leu Pro Glu Gly
65                  70                  75                  80

Cys Glu Ser Thr Asp Gln Ile Pro Ser Val Val Leu Ile Pro Asn Phe
                85                  90                  95

Leu Ser Ala Ile Asp Met Leu Gln Gln Lys Leu Glu Glu Arg Phe Glu
            100                 105                 110

Met Ile Asn Pro Arg Pro Asn Cys Ile Ile Ser Asp Lys Tyr Met Ser
        115                 120                 125

Trp Thr Gly Asp Phe Ala Asp Lys Tyr Arg Leu Pro Arg Ile Met Phe
    130                 135                 140

Asp Gly Met Ser Cys Phe Asn Glu Leu Cys Cys Asn Asn Leu Tyr Glu
145                 150                 155                 160

His Lys Val Phe Asp Gly Leu Pro Asp Ser Glu Pro Phe Val Val Leu
                165                 170                 175

Gly Leu Pro Asp Arg Val Glu Leu Thr Arg Asn Gln Leu Pro Pro Glu
            180                 185                 190

Phe Asn Pro Ser Ser Val Asp Thr Ser Ala Phe Arg Gln Arg Ala Arg
        195                 200                 205

Asp Ala Glu Val Arg Ala Tyr Gly Val Val Ile Asn Ser Phe Asp Glu
    210                 215                 220

Leu Glu Gln Glu Tyr Val Asn Glu Tyr Lys Lys Leu Arg Gly Gly Lys
225                 230                 235                 240

Val Trp Cys Ile Gly Pro Leu Ser Leu Cys Asp Ser Asp Ser Ile
                245                 250                 255

Lys Ser Gln Arg Gly Asn Val Ala Ser Ile Asn Glu Gln Gln Cys Leu
            260                 265                 270

Lys Trp Leu Asp Ser His Glu Pro Glu Ser Val Val Tyr Ala Cys Phe
        275                 280                 285

Gly Ser Leu Val Arg Ile Asn Thr Pro Gln Leu Ile Glu Leu Gly Leu
    290                 295                 300

Gly Leu Glu Ala Ser Asn Arg Pro Phe Ile Trp Val Ile Lys Ser Val
305                 310                 315                 320

His Arg Glu Lys Glu Val Glu Glu Trp Leu Ala Glu Ser Gly Phe Glu
                325                 330                 335

```
Glu Arg Val Lys His Arg Gly Leu Ile Ile Arg Gly Trp Ala Pro Gln
            340                 345                 350

Val Leu Ile Leu Ser His Pro Ser Val Gly Phe Leu Thr His Cys
            355                 360             365

Gly Trp Asn Ser Thr Leu Glu Ser Val Ser Ala Gly Val Pro Met Ile
        370                 375                 380

Thr Trp Pro Gln Phe Ala Glu Gln Phe Ile Asn Glu Lys Leu Val Val
385                 390                 395                 400

Gln Val Leu Gly Ile Gly Val Gly Val Ala Asp Ser Val Val His
                405                 410                 415

Val Gly Glu Glu Asp Arg Phe Gly Val Lys Val Lys Ser Glu Ser Val
            420                 425                 430

Lys Lys Ala Ile Glu Gln Val Met Asp Gly Gly Ile Glu Gly Asn Glu
            435                 440                 445

Arg Arg Lys Ser Val Lys Lys Leu Ala Ile Ile Ala Asn Asn Ala Ile
        450                 455                 460

Lys Glu Gly Gly Ser Ser His Leu Asn Leu Thr Leu Leu Ile Gln Asp
465                 470                 475                 480

Ile Met His His Ser Asp Thr Ser Cys Lys Glu Ser
                485                 490

<210> SEQ ID NO 3
<211> LENGTH: 1491
<212> TYPE: DNA
<213> ORGANISM: Stevia rebaudiana
<220> FEATURE:
<221> NAME/KEY: exon
<222> LOCATION: (1)..(1491)

<400> SEQUENCE: 3
```

| | | | | | | | | | | | | | | | | |
|---|---|---|---|---|---|---|---|---|---|---|---|---|---|---|---|---|
| atg | gct | tta | gaa | gaa | tca | caa | gaa | ccc | aac | caa | ctt | cac | ttt | ctt | gta | 48 |
| Met | Ala | Leu | Glu | Glu | Ser | Gln | Glu | Pro | Asn | Gln | Leu | His | Phe | Leu | Val | |
| 1 | | | | 5 | | | | | 10 | | | | | 15 | | |
| ata | ccc | tta | gga | tct | cca | ggt | cac | tat | atc | cca | acc | att | gat | tta | tcc | 96 |
| Ile | Pro | Leu | Gly | Ser | Pro | Gly | His | Tyr | Ile | Pro | Thr | Ile | Asp | Leu | Ser | |
| | | | 20 | | | | | 25 | | | | | 30 | | | |
| aaa | tta | cta | gct | caa | cat | gga | gtt | aga | gtc | acc | ata | gtc | acc | acc | ccg | 144 |
| Lys | Leu | Leu | Ala | Gln | His | Gly | Val | Arg | Val | Thr | Ile | Val | Thr | Thr | Pro | |
| | | 35 | | | | | 40 | | | | | 45 | | | | |
| gtt | aac | gcc | gtc | aga | ttc | ggg | tca | atc | ctt | gat | caa | gca | att | caa | tcg | 192 |
| Val | Asn | Ala | Val | Arg | Phe | Gly | Ser | Ile | Leu | Asp | Gln | Ala | Ile | Gln | Ser | |
| | 50 | | | | | 55 | | | | | 60 | | | | | |
| ggt | ctt | ccc | att | agt | ttt | ctt | gaa | ttt | cgg | tta | cca | tat | atg | aag | ttt | 240 |
| Gly | Leu | Pro | Ile | Ser | Phe | Leu | Glu | Phe | Arg | Leu | Pro | Tyr | Met | Lys | Phe | |
| 65 | | | | | 70 | | | | | 75 | | | | | 80 | |
| aac | ata | cca | gaa | ggt | tgt | gaa | tgc | ttg | gat | gat | gtt | cct | aat | att | ggg | 288 |
| Asn | Ile | Pro | Glu | Gly | Cys | Glu | Cys | Leu | Asp | Asp | Val | Pro | Asn | Ile | Gly | |
| | | | | 85 | | | | | 90 | | | | | 95 | | |
| tca | gcc | cat | gat | ctt | ttt | ctt | gca | cat | agt | tca | ctg | caa | caa | gaa | gtt | 336 |
| Ser | Ala | His | Asp | Leu | Phe | Leu | Ala | His | Ser | Ser | Leu | Gln | Gln | Glu | Val | |
| | | | 100 | | | | | 105 | | | | | 110 | | | |
| gaa | gaa | tat | att | gaa | aag | ctt | gat | cat | aaa | cca | agt | tgc | ata | ctt | tca | 384 |
| Glu | Glu | Tyr | Ile | Glu | Lys | Leu | Asp | His | Lys | Pro | Ser | Cys | Ile | Leu | Ser | |
| | | 115 | | | | | 120 | | | | | 125 | | | | |
| ggc | aca | tat | ctt | tta | tgg | aca | agt | gaa | act | gca | aaa | aag | ttt | cag | att | 432 |
| Gly | Thr | Tyr | Leu | Leu | Trp | Thr | Ser | Glu | Thr | Ala | Lys | Lys | Phe | Gln | Ile | |
| | 130 | | | | | 135 | | | | | 140 | | | | | |
| cca | agg | att | gtg | ttt | gat | gga | atg | aat | tgc | ttc | act | cag | atg | tgt | aac | 480 |
| Pro | Arg | Ile | Val | Phe | Asp | Gly | Met | Asn | Cys | Phe | Thr | Gln | Met | Cys | Asn | |

```
                  145                 150                 155                 160
          cat gtt tta tac atc tca aag gtg tat gaa agt gtt agt gag tca gaa       528
          His Val Leu Tyr Ile Ser Lys Val Tyr Glu Ser Val Ser Glu Ser Glu
                          165                 170                 175 tct ttt gtg tta ccc ggt ttg cct gat cgt att gaa cta aca aga tcc       576
          Ser Phe Val Leu Pro Gly Leu Pro Asp Arg Ile Glu Leu Thr Arg Ser
                          180                 185                 190 caa cta tct ttt gta ttc aat tcg ggc tcc aaa gac gtg aag gat ttc       624
          Gln Leu Ser Phe Val Phe Asn Ser Gly Ser Lys Asp Val Lys Asp Phe
                          195                 200                 205 agt gag aag ctt cgg gta tcg gag tcc gaa gcg ttt ggt ata gtt ata       672
          Ser Glu Lys Leu Arg Val Ser Glu Ser Glu Ala Phe Gly Ile Val Ile
                          210                 215                 220 aat agt ttt cat gag ttg gag caa gaa tat gtt gag gca tat caa aaa       720
          Asn Ser Phe His Glu Leu Glu Gln Glu Tyr Val Glu Ala Tyr Gln Lys
          225                 230                 235                 240 gtc aaa gaa gat aaa gct tgg tgc ata ggg cca tta tct cta tgc cac       768
          Val Lys Glu Asp Lys Ala Trp Cys Ile Gly Pro Leu Ser Leu Cys His
                          245                 250                 255 aag gat gta tcc gag aaa gtc caa aga ggt aac aag tcc tca att gac       816
          Lys Asp Val Ser Glu Lys Val Gln Arg Gly Asn Lys Ser Ser Ile Asp
                          260                 265                 270 aaa gat gaa tgc atc aag tgg ctc gat tct caa gaa aat gaa tcg gta       864
          Lys Asp Glu Cys Ile Lys Trp Leu Asp Ser Gln Glu Asn Glu Ser Val
                          275                 280                 285 atc tat gtg tgt tta ggt agc atc agt cgc ctt gag cct tca cag ctc       912
          Ile Tyr Val Cys Leu Gly Ser Ile Ser Arg Leu Glu Pro Ser Gln Leu
                          290                 295                 300 ata gag ctt gct tta ggt ctt gag tca tca aaa aga ccg ttc att tgg       960
          Ile Glu Leu Ala Leu Gly Leu Glu Ser Ser Lys Arg Pro Phe Ile Trp
          305                 310                 315                 320 gtg gtt cga gcc ggc cac aag act gag aag ata gaa aag tgg ata gat      1008
          Val Val Arg Ala Gly His Lys Thr Glu Lys Ile Glu Lys Trp Ile Asp
                          325                 330                 335 gaa gag ggg ttt gaa gag aga acc aaa gat aga ggt cta ttg atc cgc      1056
          Glu Glu Gly Phe Glu Glu Arg Thr Lys Asp Arg Gly Leu Leu Ile Arg
                          340                 345                 350 ggg tgg gct cca caa gtg cta ata ctg tca cac cct gca gtt ggt gcg      1104
          Gly Trp Ala Pro Gln Val Leu Ile Leu Ser His Pro Ala Val Gly Ala
                          355                 360                 365 ttt ttg act cac tgt ggt tgg aac tca gct ctc gaa ggg ata tct gcg      1152
          Phe Leu Thr His Cys Gly Trp Asn Ser Ala Leu Glu Gly Ile Ser Ala
                          370                 375                 380 ggt gtc cct atg gtg acg tgg cct cag ttt caa gaa caa ttt tac aat      1200
          Gly Val Pro Met Val Thr Trp Pro Gln Phe Gln Glu Gln Phe Tyr Asn
          385                 390                 395                 400 gag aag tta ctt gta caa gta tta aga att ggc gtt agt gtt ggc gcg      1248
          Glu Lys Leu Leu Val Gln Val Leu Arg Ile Gly Val Ser Val Gly Ala
                          405                 410                 415 caa aaa gtt gtg cat tgg ggt gaa gaa gaa aag tca gga gtg gta gta      1296
          Gln Lys Val Val His Trp Gly Glu Glu Glu Lys Ser Gly Val Val Val
                          420                 425                 430 aag agt gag gaa ttt agt aag gct ata gag atg atg atg gaa gat ggg      1344
          Lys Ser Glu Glu Phe Ser Lys Ala Ile Glu Met Met Met Glu Asp Gly
                          435                 440                 445 aaa gaa agt gaa gac aga aga aag aga gcc aaa gat ctt ggt aag atg      1392
          Lys Glu Ser Glu Asp Arg Arg Lys Arg Ala Lys Asp Leu Gly Lys Met
                          450                 455                 460 gca aat gaa gca gtt gaa gaa gga gga tct tct cac cgg aat atg aca      1440
```

```
                    Ala Asn Glu Ala Val Glu Gly Gly Ser Ser His Arg Asn Met Thr
                    465                 470                 475                 480 cga tta atc caa gat att agg aac cta tct agt aca agg aat tca agc         1488
Arg Leu Ile Gln Asp Ile Arg Asn Leu Ser Ser Thr Arg Asn Ser Ser
                485                 490                 495 taa                                                                      1491

<210> SEQ ID NO 4
<211> LENGTH: 496
<212> TYPE: PRT
<213> ORGANISM: Stevia rebaudiana
<220> FEATURE:
<221> NAME/KEY: PEPTIDE
<222> LOCATION: (1)..(496)

<400> SEQUENCE: 4

Met Ala Leu Glu Glu Ser Gln Glu Pro Asn Gln Leu His Phe Leu Val
1               5                   10                  15

Ile Pro Leu Gly Ser Pro Gly His Tyr Ile Pro Thr Ile Asp Leu Ser
            20                  25                  30

Lys Leu Leu Ala Gln His Gly Val Arg Val Thr Ile Val Thr Thr Pro
        35                  40                  45

Val Asn Ala Val Arg Phe Gly Ser Ile Leu Asp Gln Ala Ile Gln Ser
    50                  55                  60

Gly Leu Pro Ile Ser Phe Leu Glu Phe Arg Leu Pro Tyr Met Lys Phe
65                  70                  75                  80

Asn Ile Pro Glu Gly Cys Glu Cys Leu Asp Asp Val Pro Asn Ile Gly
                85                  90                  95

Ser Ala His Asp Leu Phe Leu Ala His Ser Ser Leu Gln Gln Glu Val
            100                 105                 110

Glu Glu Tyr Ile Glu Lys Leu Asp His Lys Pro Ser Cys Ile Leu Ser
        115                 120                 125

Gly Thr Tyr Leu Leu Trp Thr Ser Glu Thr Ala Lys Lys Phe Gln Ile
    130                 135                 140

Pro Arg Ile Val Phe Asp Gly Met Asn Cys Phe Thr Gln Met Cys Asn
145                 150                 155                 160

His Val Leu Tyr Ile Ser Lys Val Tyr Glu Ser Val Ser Glu Ser Glu
                165                 170                 175

Ser Phe Val Leu Pro Gly Leu Pro Asp Arg Ile Glu Leu Thr Arg Ser
            180                 185                 190

Gln Leu Ser Phe Val Phe Asn Ser Gly Ser Lys Asp Val Lys Asp Phe
        195                 200                 205

Ser Glu Lys Leu Arg Val Ser Glu Ser Glu Ala Phe Gly Ile Val Ile
    210                 215                 220

Asn Ser Phe His Glu Leu Glu Gln Glu Tyr Val Glu Ala Tyr Gln Lys
225                 230                 235                 240

Val Lys Glu Asp Lys Ala Trp Cys Ile Gly Pro Leu Ser Leu Cys His
                245                 250                 255

Lys Asp Val Ser Glu Lys Val Gln Arg Gly Asn Lys Ser Ser Ile Asp
            260                 265                 270

Lys Asp Glu Cys Ile Lys Trp Leu Asp Ser Gln Glu Asn Glu Ser Val
        275                 280                 285

Ile Tyr Val Cys Leu Gly Ser Ile Ser Arg Leu Glu Pro Ser Gln Leu
    290                 295                 300

Ile Glu Leu Ala Leu Gly Leu Glu Ser Ser Lys Arg Pro Phe Ile Trp
305                 310                 315                 320
```

```
Val Val Arg Ala Gly His Lys Thr Glu Lys Ile Glu Lys Trp Ile Asp
                325             330             335

Glu Glu Gly Phe Glu Glu Arg Thr Lys Asp Arg Gly Leu Leu Ile Arg
            340             345             350

Gly Trp Ala Pro Gln Val Leu Ile Leu Ser His Pro Ala Val Gly Ala
            355             360             365

Phe Leu Thr His Cys Gly Trp Asn Ser Ala Leu Glu Gly Ile Ser Ala
        370             375             380

Gly Val Pro Met Val Thr Trp Pro Gln Phe Gln Glu Gln Phe Tyr Asn
385             390             395             400

Glu Lys Leu Leu Val Gln Val Leu Arg Ile Gly Val Ser Val Gly Ala
            405             410             415

Gln Lys Val Val His Trp Gly Glu Glu Glu Lys Ser Gly Val Val Val
            420             425             430

Lys Ser Glu Glu Phe Ser Lys Ala Ile Glu Met Met Met Glu Asp Gly
            435             440             445

Lys Glu Ser Glu Asp Arg Arg Lys Arg Ala Lys Asp Leu Gly Lys Met
        450             455             460

Ala Asn Glu Ala Val Glu Glu Gly Gly Ser Ser His Arg Asn Met Thr
465             470             475             480

Arg Leu Ile Gln Asp Ile Arg Asn Leu Ser Ser Thr Arg Asn Ser Ser
                485             490             495
```

STEVIOL GLYCOSYLTRANSFERASES AND GENES ENCODING THE SAME

Polynucleotides encoding corresponding polypeptides capable of glycosylating steviol at its C-19 position to produce a steviol glycoside, expression vectors and host cells containing such a polynucleotide, and methods of producing the steviol glycoside using such polynucleotide are described. The polypeptides readily convert steviol with high specificity to steviol-19-O-glycoside, which can serve as a precursor for other desirable steviol glycosides.

INCORPORATION OF SEQUENCE LISTING

Incorporated by reference herein is the material contained in the ASCII text file entitled "Sequence Listing for Steviol Glycosyltransferases and Genes Encoding the Same," having a file size of 23,000 bytes and created on Aug. 13, 2020.

BACKGROUND

Steviol glycosides are natural, non-caloric sweeteners produced in *Stevia rebaudiana* and have important applications in the food and beverage industry. The biosynthesis of steviol glycosides requires a UDP-glycosyltransferase (UGT) enzyme, which mediates the transfer of glycosyl residues from nucleotide sugars to steviol to produce a steviol glycoside. However, not all UDP-glycosyltransferases convert steviol to a desirable steviol glycoside, much less with high specificity. Accordingly, there is a need for UDP-glycosyltransferases capable of converting steviol to a desirable steviol glycoside with high specificity, particularly UDP-glycosyltransferases encoded by polynucleotides adapted for expression by a recombinant host containing such a polynucleotide.

SUMMARY

According to one aspect of this disclosure, a polynucleotide is selected from a polynucleotide having at least 80% identity to the nucleotide sequence of SEQ ID NO: 1, a polynucleotide that includes a heterologous regulatory element operably linked to a polynucleotide sequence encoding a polypeptide comprising an amino acid sequence having at least 80% identity to SEQ ID NO: 2, a polynucleotide having at least 80% identity to the nucleotide sequence of SEQ ID NO: 3; or a polynucleotide comprising a heterologous regulatory element operably linked to a polynucleotide sequence encoding a polypeptide comprising an amino acid sequence having at least 80% identity to SEQ ID NO: 4.

The polynucleotide having at least 80% identity to the nucleotide sequence of SEQ ID NO: 1 or SEQ ID NO: 3 may encode a polypeptide capable of glycosylating steviol at its C-19 position to produce steviol-19-O-glycoside and the polypeptide that includes an amino acid sequence having at least 80% identity to SEQ ID NO: 2 or SEQ ID NO: 4 may be capable of glycosylating steviol at its C-19 position to produce steviol-19-O-glycoside.

In some embodiments, the polynucleotide may have greater than 80% identity to the nucleotide sequence of SEQ ID NO: 1 or may be a polynucleotide that includes a heterologous regulatory element operably linked to a polynucleotide sequence encoding a polypeptide comprising an amino acid sequence having greater than 80% identity to SEQ ID NO: 2. For example, the polynucleotide may be the polynucleotide including the heterologous regulatory element operably linked to the polynucleotide that includes an amino acid sequence having greater than 80% identity to SEQ ID NO: 2. In some embodiments, the polynucleotide may have greater than 80% identity to the nucleotide sequence of SEQ ID NO: 3 or may be a polynucleotide that includes a heterologous regulatory element operably linked to a polynucleotide sequence encoding a polypeptide comprising an amino acid sequence having greater than 80% identity to SEQ ID NO: 4. For example, the polynucleotide may be the polynucleotide including the heterologous regulatory element operably linked to the polynucleotide that includes an amino acid sequence having greater than 80% identity to SEQ ID NO: 4.

According to another aspect, a transcription template includes a polynucleotide selected from a polynucleotide having at least 80% identity to the nucleotide sequence of SEQ ID NO: 1, a polynucleotide that includes a heterologous regulatory element operably linked to a polynucleotide sequence encoding a polypeptide comprising an amino acid sequence having at least 80% identity to SEQ ID NO: 2, a polynucleotide having at least 80% identity to the nucleotide sequence of SEQ ID NO: 3; or a polynucleotide comprising a heterologous regulatory element operably linked to a polynucleotide sequence encoding a polypeptide comprising an amino acid sequence having at least 80% identity to SEQ ID NO: 4. This transcription template may be adapted for in vitro transcription and translation in a cell-free system to produce a polypeptide encoded by the polynucleotide. The transcription template may be; e.g., a linearized plasmid, PCR product, or cDNA converted to double-stranded template.

According to another aspect, an expression vector includes a polynucleotide selected from a polynucleotide having at least 80% identity to the nucleotide sequence of SEQ ID NO: 1, a polynucleotide that includes a heterologous regulatory element operably linked to a polynucleotide sequence encoding a polypeptide comprising an amino acid sequence having at least 80% identity to SEQ ID NO: 2, a polynucleotide having at least 80% identity to the nucleotide sequence of SEQ ID NO: 3; or a polynucleotide comprising a heterologous regulatory element operably linked to a polynucleotide sequence encoding a polypeptide comprising an amino acid sequence having at least 80% identity to SEQ ID NO: 4. This expression vector may be contained within a recombinant host cell capable of expressing a UDP-glycosyltransferase from the polynucleotide, the recombinant host cell selected from the group consisting of a bacterial cell, a fungal cell, an animal cell (e.g., a mammalian cell or an insect cell), or a plant cell.

According to another aspect, a method for producing a steviol glycoside is disclosed. The method includes culturing a recombinant host cell. The recombinant host cell contains an expression vector that includes a polynucleotide selected from a polynucleotide having at least 80% identity to the nucleotide sequence of SEQ ID NO: 1, a polynucleotide that includes a heterologous regulatory element operably linked to a polynucleotide sequence encoding a polypeptide comprising an amino acid sequence having at least 80% identity to SEQ ID NO: 2, a polynucleotide having at least 80% identity to the nucleotide sequence of SEQ ID NO: 3, or a polynucleotide comprising a heterologous regulatory element operably linked to a polynucleotide sequence encoding a polypeptide that includes an amino acid sequence having at least 80% identity to SEQ ID NO: 4.

The recombinant host cell is capable of expressing a UDP-glycosyltransferase from the polynucleotide and is selected from the group consisting of a bacterial cell, a fungal cell, an animal cell (e.g., a mammalian cell or an insect cell), or a plant cell. In one embodiment, the method further includes producing steviol-19-O-glycoside by contacting the UDP-glycosyltransferase produced by the recombinant host cell with at least steviol and a nucleotide sugar. In this embodiment, contacting the UDP-glycosyltransferase produced by the host cell with at least steviol and a nucleotide sugar may include incubating the recombinant host cell with at least the steviol and the nucleotide sugar, and the method may further include allowing the UDP-glycosyltransferase to glycosylate steviol at its C-19 position to produce steviol-19-O-glycoside and extracting the steviol-19-O-glycoside from the recombinant host cell. In this embodiment, the nucleotide sugar is selected from the group consisting of UDP-glucose and UDP-rhamnose. However, other suitable nucleotide sugars may be used.

According to another aspect, another method for producing a steviol glycoside is disclosed. The method includes contacting a composition comprising steviol with a recombinant UDP-glycosyltransferase, the recombinant UDP-glycosyltransferase comprising an amino acid sequence having at least 80% identity to SEQ ID NO: 2 or SEQ ID NO: 4. In an embodiment, the composition further includes a nucleotide sugar. The nucleotide sugar in this embodiment may be selected from the group consisting of UDP-glucose and UDP-rhamnose. However, other nucleotide sugars may be used. In another embodiment, the recombinant UDP-glycosyltransferase glycosylates steviol at a C-19 position to produce steviol-19-O-glycoside.

According to another aspect, another recombinant host cell is disclosed. The recombinant host cell has a modified level of a UDP-glycosyltransferase relative to a wild-type cell of the same taxon. The recombinant host cell is capable of producing steviol-19-O-glycoside when the UDP-glycosyltransferase is contacted with at least steviol and a nucleotide sugar, and comprises a polynucleotide selected from: a polynucleotide having at least 80% identity to the nucleotide sequence of SEQ ID NO: 1; a polynucleotide comprising a heterologous regulatory element operably linked to a polynucleotide sequence encoding a polypeptide comprising an amino acid sequence having at least 80% identity to SEQ ID NO: 2; a polynucleotide having at least 80% identity to the nucleotide sequence of SEQ ID NO: 3; or a polynucleotide comprising a heterologous regulatory element operably linked to a polynucleotide sequence encoding a polypeptide comprising an amino acid sequence having at least 80% identity to SEQ ID NO: 4. The recombinant host cell may be further capable of producing steviol and the nucleotide sugar. In this embodiment, the recombinant host cell may have a modified level of at least one of steviol, the nucleotide sugar, and steviol-19-O-glycoside relative to the wild-type cell of the same taxon. The recombinant host cell in this embodiment may be incorporated into a multicellular structure, which may be plant tissue, such as plant issue of a whole plant of the species Stevia rebaudiana.

BRIEF DESCRIPTION OF THE DRAWINGS

The following description accompanies the drawings, all given by way of non-limiting examples that may be useful to understand how the described process and system may be embodied. In addition, the drawings and elements shown in the drawings are not necessarily or intended to be to scale.

BRIEF DESCRIPTION OF SEQUENCES

Figure 1:
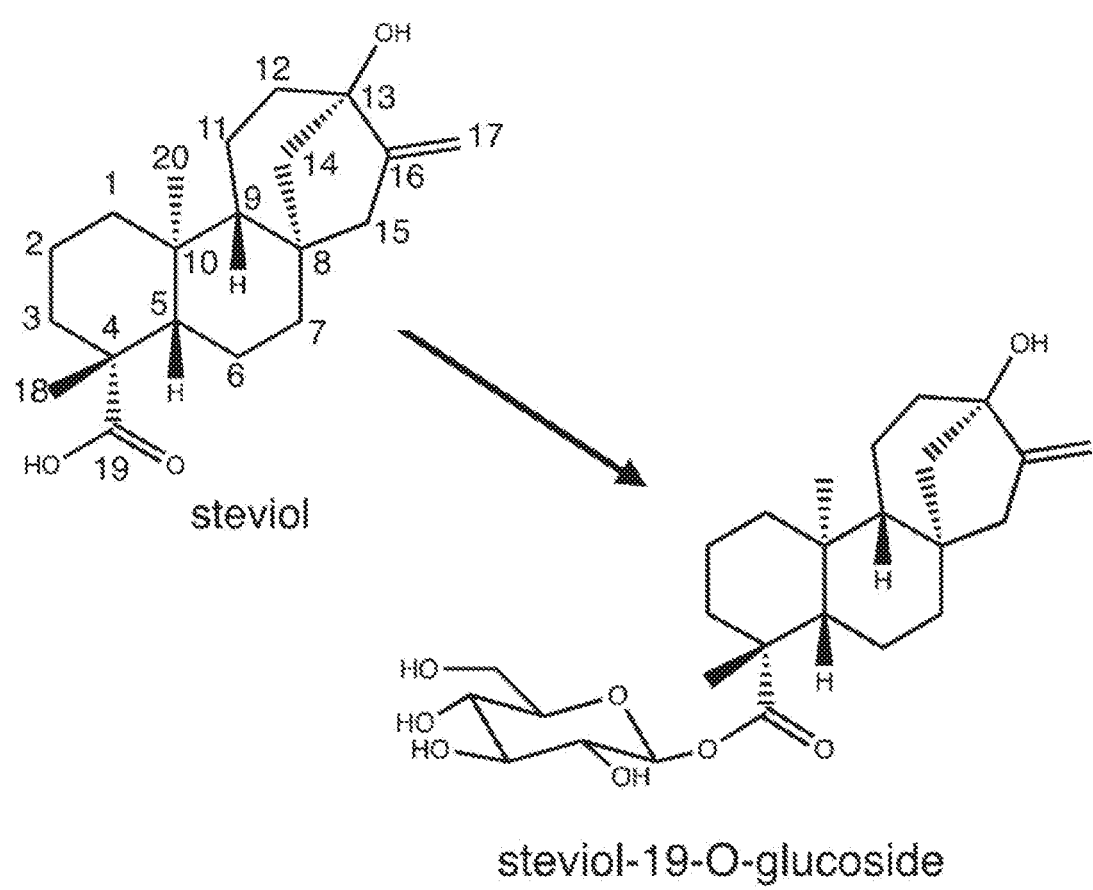
FIG. 1 schematically shows the conversion of steviol to steviol-19-O-glycoside.

SEQ ID NO: 1 is a non-naturally occurring DNA coding sequence encoding UDP-glycosyltransferase UGT73C6_49505.

SEQ ID NO: 2 is an amino acid sequence of UDP-glycosyltransferase UGT73C6_49505.

SEQ ID NO: 3 is a non-naturally occurring DNA coding sequence encoding UDP-glycosyltransferase UGT73C6_49903.

SEQ ID NO: 4 is an amino acid sequence of UDP-glycosyltransferase UGT73C6_49903.

DESCRIPTION

Polynucleotides encoding corresponding polypeptides capable of glycosylating steviol at its C-19 position to produce a steviol glycoside, expression vectors and host cells containing such a polynucleotide, and methods of producing the steviol glycoside using such polynucleotide are described.

Definitions

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides, conservatively modified variants thereof, complementary sequences, and degenerate codon substitutions that have similar binding properties as the reference nucleic acid and are metabolized in a manner similar to naturally occurring nucleotides.

The terms "nucleic acid," "nucleic acid molecule," "nucleic acid fragment," "nucleic acid sequence or segment," or "polynucleotide" are used interchangeably.

The term "vector" refers to any genetic element, such as a plasmid, phage, transposon, cosmid, chromosome, virus, virion, etc., which is capable of replication when associated with the proper control elements, such as a helper virus, and which can transfer gene sequences between cells. Thus, the term includes cloning and expression vehicles, as well as replication-defective viral vectors. Numerous types of vectors exist and are well known in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous polypeptide indicates that the polypeptide comprises two or more subsequences that are not found in the same relationship to each other in nature (e.g., a fusion polypeptide).

The term "variant" of a molecule is a sequence that is substantially similar to the sequence of the reference molecule. For nucleotide sequences, variants include those sequences that, because of the degeneracy of the genetic code, encode the identical amino acid sequence of the reference protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the reference protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99% sequence identity to the reference (endogenous) nucleotide sequence.

The term "conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence, such as an RNA nucleotide complementary to a DNA nucleotide. Preferably, the substantial identity exists over a region that is at least about 6-7 amino acids or 25 nucleotides in length.

An example of an algorithm that is suitable for determining percent sequence identity and sequence similarity is the BLAST algorithm, which is described in Altschul et al., 1977, Nuc. Acids Res. 25:3389-3402. BLAST is used, with the parameters described herein, to determine percent sequence identity for the nucleic acids and proteins of the invention. Software for performing BLAST analysis is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA, 89:10915 (1989)) alignments (B) of 50, expectation (E) of 10, M=5, N=−4, and a comparison of both strands. The TBLASTN program (for translated nucleotide sequences compared to protein) uses as defaults a wordlength (W) of X, an expectation (E) or X, M=X, N=X and a comparison of both strands The BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The practice of the disclosure will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985);

Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as Advances in Immunology.

Polypeptides

Polypeptides of the present disclosure glycosylate steviol at its C-19 position to produce a steviol glycoside. In some embodiments, the polypeptides may include amino acid substitutions, deletions, truncations, and insertions and still function to glycosylate steviol at its C-19 position to produce a steviol glycoside. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873,192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Recombinant Expression Vectors and Host Cells

In some embodiments, vectors, for example, recombinant expression vectors, containing a nucleic acid encoding a polypeptide to produce a steviol glycoside are disclosed. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Examples of vectors are plasmids (e.g., DNA plasmids or RNA plasmids), autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pCIneo vectors (Promega) for expression in mammalian cells; pLenti4N5-DEST™, pLenti6N5-DEST™, and pLenti6.2N5-GW/lacZ (Invitrogen) for lentivirus-mediated gene transfer and expression in mammalian cells. In certain embodiments, useful viral vectors include, e.g., replication defective retroviruses and lentiviruses.

The recombinant expression vectors can include a nucleic acid encoding a polypeptide to produce a steviol glycoside described herein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. The "control elements" or "regulatory sequences" present in an expression vector are those non-translated regions of the vector—origin of replication, selection cassettes, promoters, enhancers, translation initiation signals (Shine Dalgarno sequence or Kozak sequence), introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 1,000-5,000 bases upstream from the start of transcription, a CNCAAT region where N may be any nucleotide.

The term "enhancer" refers to a segment of DNA which contains sequences capable of providing enhanced transcription and in some instances may function independent of their orientation relative to another control sequence. An enhancer may function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide—of interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments of the disclosure in which a recombinant host cell is a plant cell include, but are not limited to, those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. Molecular and App. Gen., 1:483 498 (1982), the entirety of which is hereby incorporated herein to the extent it is consistent herewith), and the promoter of the chlorophyll a/b binding protein. These two promoters are known to be light-induced in plant cells (see, for example, Genetic Engineering of Plants, an Agricultural Perspective, A. Cashmore, Plenum, N.Y. (1983), pages 29 38; Coruzzi, G. et al., The Journal of Biological Chemistry, 258:1399 (1983), and Dunsmuir, P. et al., Journal of Molecular and Applied Genetics, 2:285 (1983), each of which is hereby incorporated herein by reference to the extent they are consistent herewith).

Illustrative ubiquitous expression control sequences suitable for use in particular embodiments of the disclosure a recombinant host cell is a microbial host cell include, but are not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *Escherichia coli*).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments described herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), lac operon promoter (inducible by isopropyl β-d-1-thiogalactopyranoside (IPTG)), the "Gene-Switch" mifepristone-regulatable system (Sirin et al., 2003, Gene, 323:67), the cumate-inducible gene switch (WO 2002/088346), tetracycline-dependent regulatory systems, etc.

Conditional expression may also be achieved by using a site specific DNA recombinase. According to certain embodiments of the disclosure the vector comprises at least one (typically two) site(s) for recombination mediated by a site specific recombinase. As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present disclosure include, but are not limited to: Cre, Int, IHF, Xis, Flp, Fis, Hin, Gin, φC31, Cin, Tn3 resolvase, TndX, XerC, XerD, TnpX, Hjc, Gin, SpCCEI, and ParA.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility and/or stability of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari, et al., (1987) EMBO J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

In some embodiments, host cells into which a nucleic acid molecule encoding a polypeptide to produce a steviol glycoside is introduced may be used. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide to produce a steviol glycoside or fusion protein can be expressed in plant cells, bacterial cells such as *E. coli*, insect cells, yeast or mammalian cells (such as hematopoietic cells, leukocytes, K562 cells, 293T cells, human umbilical vein endothelial cells (HUVEC), human microvascular endothelial cells (HMVEC), Chinese hamster ovary cells (CHO) or COS cells). Other suitable host cells are known to those skilled in the art. A host cell, such as a prokaryotic or eukaryotic host cell in culture, may be used to produce (i.e., express) a polypeptide to produce a steviol glycoside.

Turning to FIG. 1, the conversion of steviol to steviol-19-O-glycoside is shown. Steviol-19-O-glycoside is a precursor to numerous other steviol glycosides including but not limited to rebaudiana A (Reb A), rebusoside, stevioside, rebaudiana C (Reb C), rebaudiana D (Reb D), rebaudiana M (Reb M), rebaudiana J (Reb J), rebaudiana B (Reb B), rebaudiana G (Reb G), rebaudiana F (Reb F), and dulcoside A, one or more of which are commercially valuable as a non-caloric sweetener for foods and beverages. The conversion of steviol to steviol-19-O-glycoside is catalyzed by a UGT that glycosylates steviol at its C-19 position in the presence of a nucleotide sugar (e.g., uridine diphosphate sugar), such as UDP-glucose or UDP-rhamnose.

The present disclosure is directed to non-naturally occurring polynucleotides that encode two such UGT enzymes: UGT73C6_49505 and UGT73C6_49903. The present disclosure is further directed to polynucleotides that include a heterologous regulatory element operably linked to a polynucleotide sequence encoding UGT73C6_49505 and UGT73C6_49903. Both UGT73C6_49505 and UGT73C6_49903 have been found to readily convert steviol to steviol-19-O-glycoside with high specificity and may be used, for example, in bioconversion strategies and bioengineering strategies for the production of high-value steviol glycosides. The polynucleotides of the present disclosure and applications thereof are discussed in further detail below.

Polynucleotides

Two UGT enzymes UGT73C6_49505 and UGT73C6_49903 have been identified in a high-Reb C variety of Stevia rebaudiana, isolated the gene sequences for UGT73C6_49505 and UGT73C6_49903 from this variety, and produced corresponding cDNA and amino acid sequences. The DNA coding sequence encoding UGT73C6_49505 is shown in SEQ ID NO: 1 and the amino acid sequence of UGT73C6_49505 is shown in SEQ ID NO: 2. The DNA coding sequence encoding UGT73C6_49903 is shown in SEQ ID NO: 3 and the amino acid sequence of UGT73C6_49903 is shown in SEQ ID NO: 4.

It should be understood that, in any given application described herein (e.g., an expression vector), a nucleotide sequence having at least 80% identity to SEQ ID NO: 1 or a polynucleotide comprising a heterologous regulatory element operably linked to a polynucleotide sequence encoding a polypeptide comprising the amino acid sequence having at least 80% identity to SEQ ID NO: 2 may be substituted for a nucleotide sequence having at least 80% identity to SEQ ID NO: 3 or a polynucleotide comprising a heterologous regulatory element operably linked to a polynucleotide sequence encoding a polypeptide having at least 80% identity to the amino acid sequence of SEQ ID NO: 4, and vice versa. That is, enzymes UGT73C6_49505 and UGT73C6_49903 have similar activity and may be used substantially interchangeably. Such polynucleotides may be produced using known commonly-known synthesis and genetic engineering techniques and expressed as a recombinant protein in a host organism or in an in vitro cell-free system.

In some examples, the polynucleotides and amino acid sequences described herein may have greater than 80% identity to one of SEQ ID NOs: 1-4, such as 85%, 90%, 95%, 100%, or approximations thereof. For the sake of clarity, an embodiment described as including or using the nucleotide sequence of SEQ ID NOs: 1 or SEQ ID NO: 3 should be understood to respectively include a polynucleotide having at least 80% identity to the nucleotide sequence of SEQ ID NO: 1 or SEQ ID NO: 3. Similarly, embodiments described as using or including the amino acid sequence of SEQ ID NO: 2 or SEQ ID NO: 4 should be understood to respectively include a polynucleotide comprising a heterologous regulatory element operably linked to a polynucleotide sequence encoding a polypeptide comprising an amino acid sequence having at least 80% identity to the amino acid sequence of SEQ ID NO: 2 or SEQ ID NO: 4.

Expression Vectors and Recombinant Hosts Containing the Polynucleotides

The DNA coding sequence of SEQ ID NO: 1 or SEQ ID NO: 3 or a polynucleotide that includes a heterologous regulatory element operably linked to a polynucleotide sequence encoding a polypeptide comprising the amino acid sequence of SEQ ID NO: 2 or SEQ ID NO: 4 may be inserted into an expression vector using standard techniques.

Such expression vectors may be tailored for expression of UGT73C6_9505 or UGT73C6_49903 in a particular type of recombinant host cell or multicellular organism that includes one or more such recombinant host cells by incorporation of suitable regulatory sequences such as enhancers, promoters, 5' and/or 3' UTRs. The recombinant host cell may be selected from a bacterial cell, a fungal cell, an animal cell (e.g., a mammalian cell or an insect cell), or a plant cell. Example recombinant host cells may include strains of E. coli, Saccharomyces species, algal cells, and the like. Further example host cells may be selected from plant cells from plants such as cereal crops such as rice, rye, sorghum, millet, wheat, maize, and barley. The plant may be a non-cereal monocot such as asparagus, banana, or onion. The plant also may be a dicot such as stevia (Stevia rebaudiana), soybean, cotton, sunflower, pea, geranium, spinach, or tobacco. A multicellular organism of such embodiments may be a suitable plant; e.g., any suitable cereal plant, non-cereal monocot, or dicot.

The expression vectors containing the DNA coding sequence of SEQ ID NO: 1 or SEQ ID NO: 3 or a polynucleotide that includes a heterologous regulatory element operably linked to a polynucleotide sequence encoding a polypeptide comprising the amino acid sequence of SEQ ID NO: 2 or SEQ ID NO: 4 may be introduced into the recombinant host cell using known suitable techniques for introducing exogenous polynucleotides into the type of cell.

In other examples, the DNA coding sequences of SEQ ID NO: 1 or SEQ ID NO: 3 or a polynucleotide that includes a heterologous regulatory element operably linked to a polynucleotide sequence encoding a polypeptide comprising the amino acid sequences of SEQ ID NO: 2 or SEQ ID NO: 4 may be used in a bioengineering strategy for expression of UGT73C6_49505 or UGT73C6_49903 in multicellular plants.

Methods of Producing Steviol Glycosides Via the Polynucleotides

In some embodiments, steviol-19-O-glycoside may be produced in vivo within a recombinant host cell containing an expression vector as described above. The recombinant host cell may be cultured under conditions in which the cell expresses recombinant UGT73C6_49505 or UGT73C6_49903. Under the culture conditions, the recombinant host cell is incubated with a substrate that contains steviol and a nucleotide sugar, such as UDP-glucose or UDP-rhamnose. The UGT73C6_49505 or UGT73C6_49903 expressed by the cell glycosylates steviol at its C-19 position to produce steviol-19-O-glycoside. The steviol-19-O-glycoside then may be extracted from the recombinant host cell and processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A.

In other embodiments, the recombinant host cell containing an expression vector as described above may be cultured under conditions in which the cell expresses recombinant UGT73C6_49505 or UGT73C6_49903. The UGT73C6_49505 or UGT73C6_49903 then may be extracted from the host cell and combined with steviol and a nucleotide sugar such as UDP-glucose or UDP-rhamnose to produce steviol-19-O-glycoside. The steviol-19-O-glycoside obtained in this manner also may be processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A.

In other embodiments, the recombinant host cell containing an expression vector as described above may be cultured under conditions in which the cell expresses recombinant UGT73C6_49505 or UGT73C6_49903 at a modified level relative to a wild-type cell of the same taxon. In such other embodiments, the recombinant host cell is capable of producing steviol-19-O-glycoside when the recombinant UGT73C6_49505 or UGT73C6_49903 is contacted with at least steviol and a nucleotide sugar such as UDP-glucose or UDP-rhamnose. The recombinant host cell may be further capable of producing the steviol and the nucleotide sugar. Where this is the case, the recombinant host cell may produce the steviol and/or the nucleotide sugar at a modified level relative to the wild-type cell of the same taxon. The steviol-19-O-glycoside obtained from the recombinant host cell of this embodiment may be processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A. Optionally, the recombinant host cell of this embodiment may be incorporated into a multicellular structure, such plant tissue; e.g., tissue of a whole plant of the species Stevia rebaudiana or another suitable species.

In still other embodiments, a transcription template as described above (e.g., a linearized plasmid, PCR product, or cDNA converted to double-stranded template) may be used in an in vitro reaction to produce recombinant UGT73C6_49505 or UGT73C6_49903. The UGT73C6_49505 or UGT73C6_49903 produced in this manner may be combined with steviol and a nucleotide sugar such as UDP-glucose or UDP-rhamnose to produce steviol-19-O-glycoside. The steviol-19-O-glycoside obtained in this manner also may be processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A.

In still other embodiments, steviol-19-O-glycoside may be produced in vivo within a multicellular organism (e.g., a host plant) produced via a bioengineering strategy to bear the DNA coding sequences of SEQ ID NO: 1 or SEQ ID NO: 3 or a polynucleotide that includes a heterologous regulatory element operably linked to a polynucleotide sequence encoding a polypeptide comprising the amino acid sequences of SEQ ID NO: 2 or SEQ ID NO: 4. The host plant may be grown under conditions in which it expresses recombinant UGT73C6_49505 or UGT73C6_49903. Under the growth conditions, the host plant is provided with a substrate that contains steviol and a nucleotide sugar, such as UDP-glucose or UDP-rhamnose. The UGT73C6_49505 or UGT73C6_49903 expressed by the host plant glycosylates steviol at its C-19 position to produce steviol-19-O-glycoside. The steviol-19-O-glycoside then may be extracted from the host plant and processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A.

In still other embodiments, a multicellular organism (e.g., a host plant) produced via a bioengineering strategy as described above may be grown under conditions in which the cell expresses recombinant UGT73C6_49505 or UGT73C6_49903. The UGT73C6_49505 or UGT73C6_49903 then may be extracted from the host plant and combined with steviol and a nucleotide sugar such as UDP-glucose or UDP-rhamnose to produce steviol-19-O-glycoside. The steviol-19-O-glycoside obtained in this manner also may be processed and/or used as desired, for example, as a precursor to a steviol glycoside sweetener such as Reb A, rebusoside, stevioside, Reb C, Reb D, Reb M, Reb J, Reb B, Reb G, Reb F, and dulcoside A.

In some embodiments, inbred Stevia rebaudiana plant lines may be identified that include a modified level of steviol glycosides relative to a conventional Stevia rebaudiana plant, plant material or seed, wherein the inbred Stevia rebaudiana plant line includes one or more desired mutant alleles of a gene encoding the UDP-glycosyltransferase UGT73C6_49505 or a gene encoding the UDP-glycosyltransferase UGT73C6_49903. In some embodiments, the inbred Stevia rebaudiana plant lines may have a trait of accumulating a desired steviol glycoside chemical profile. In some embodiments, Stevia rebaudiana plant lines having one or more genetic modifications to introduce a gene encoding the UDP-glycosyltransferase UGT73C6_49505 or a gene encoding the UDP-glycosyltransferase UGT73C6_49903 may be screened to determine plant lines having the desired amount of expression of the UDP-glycosyltransferase relative to a wild type Stevia rebaudiana plant line. The amount of expression may be increased or decreased relative to the wild type plant line. In some embodiments, the amount of expression may be increased relative to the wild type plant line.

Example Expression of UGT73C6 49505 and UGT73C6 49903 and Characterization of Enzyme Activity The following description illustrates one exemplary method of expressing the recombinant UGT73C6_49505 and UGT73C6_49903 described above and characterizing their enzyme activity.

Figure 2:
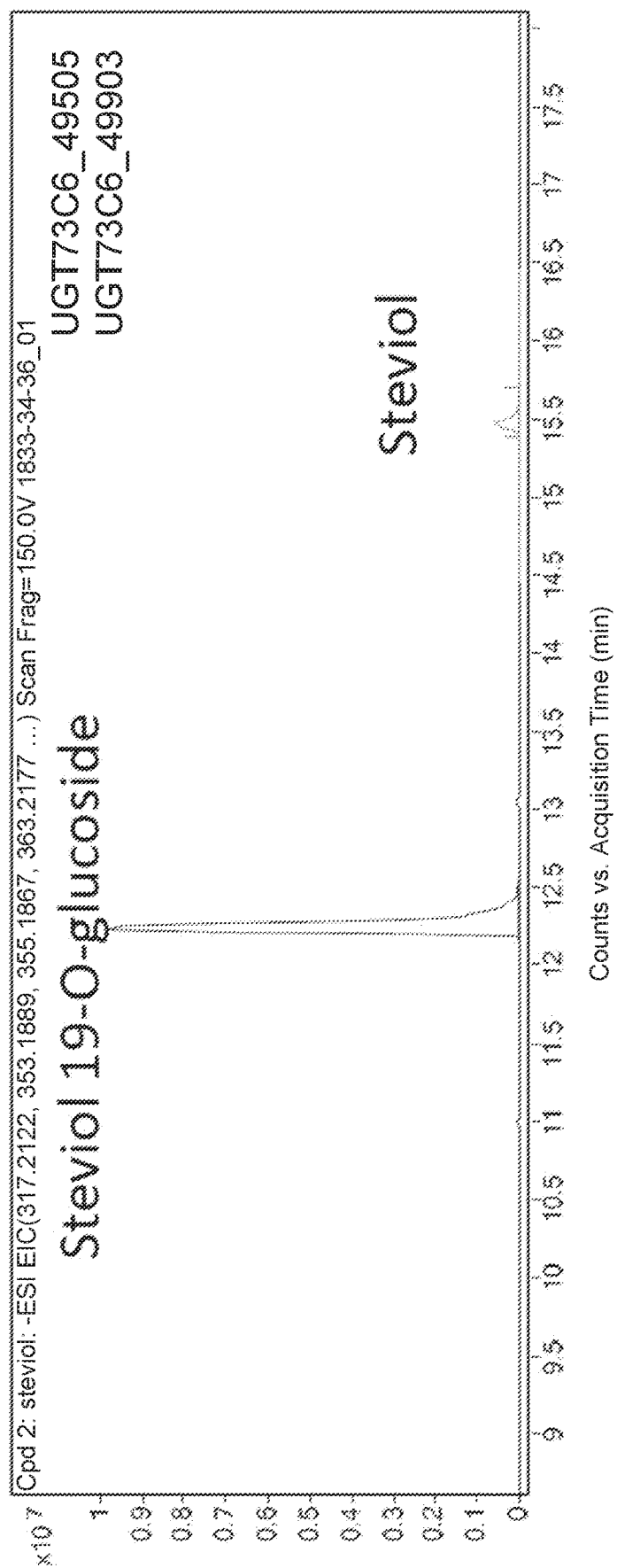
FIG. 2 shows the results of an enzyme assay establishing the steviol-19-O-glucosyltransferase activity of a UDP-glycosyltransferase expressed by a polynucleotide of this disclosure.

The DNA coding sequence of SEQ ID NO: 1 or SEQ ID NO: 3 were inserted into pE-SUMOpro protein expression plasmid (available at LifeSensor.com) for expression in E coli using standard molecular cloning techniques. UGT73C6_49505 and UGT73C6_49903 were heterologously-expressed in E. coli. Expression was observed with SDS-Page and a Western Blot using a commercially-available anti-His tag antibody. The protein extract from these cells were collected by following the protocol using B-PER bacteria protein extraction reagent (Thermo Scientific) and used for activity assays. Each enzyme reaction contained 50 mM potassium phosphate buffer pH 7.2, 3 mM $MgCl_2$, 14 mM β-mercaptoethanol, 50 μM of steviol glycoside substrate (such as steviol), equal amount of 500 μM nucleotide sugar (such as UDP-glucose), and 10 μl of the crude protein extract. The reactions were incubated at 30° C. for 2 hr., followed by adding 2.5× volume of acetonitrile to terminate the reaction. After 20 min of centrifugation at top speed, the supernatant was analyzed on LC-MS. The results of the analysis of the enzyme reactions are illustrated in FIG. 2 and summarized below in Tables 1 and 2.

TABLE 1

| Peak Area | |
|---|---|
| Steviol | Steviol-19-O-glycoside |
| UGT73C6_49505 (pXL1133) | |
| 4668408 | 48311704 |
| UGT73C6_49903 (pXL1134) | |
| 5529828 | 13261990 |
| Denatured Enzyme Control | |
| 5779141 | 0 |

TABLE 2

| Amount (ng) | |
|---|---|
| Steviol | Steviol-19-O-glycoside |
| UGT73C6_49505 (pXL1133) | |
| 2877.12 | 795.37 |
| UGT73C6_49903 (pXL1134) | |
| 3408.00 | 218.34 |
| Denatured Enzyme Control | |
| 3561.65 | n/a |

While the concepts of the present disclosure are susceptible to various modifications and alternative forms, it should be understood, however, that there is no intent to limit the concepts of the present disclosure to the particular disclosed forms; the intention is to cover all modifications, equivalents, and alternatives falling within the spirit and scope of the invention as defined by the claims.

The invention claimed is:

1. An isolated polynucleotide selected from:
   a polynucleotide comprising a heterologous regulatory element operably linked to a polynucleotide sequence encoding a polypeptide comprising the amino acid sequence of SEQ ID NO: 2; or
   a polynucleotide comprising a heterologous regulatory element operably linked to a polynucleotide sequence encoding a polypeptide comprising the amino acid sequence of SEQ ID NO: 4.

2. The polynucleotide of claim 1, wherein the polynucleotide sequence that encodes the polypeptide of the amino acid sequence of SEQ ID NO: 2 comprises the SEQ ID NO: 1 or wherein the polynucleotide sequence that encodes the polypeptide of the amino acid sequence of SEQ ID NO: 4 comprises the SEQ ID NO: 3.

3. A transcription template comprising the polynucleotide of claim 1, wherein the transcription template is adapted for in vitro transcription in a cell-free system.

4. An expression vector comprising the polynucleotide of claim 1.

5. The expression vector of claim 4, contained within a recombinant host cell capable of expressing a UDP-glycosyltransferase from the polynucleotide, the recombinant host cell selected from the group consisting of a bacterial cell, a fungal cell, an animal cell, or a plant cell.

6. A method for producing a steviol glycoside, the method comprising culturing the recombinant host cell of the claim 5 under conditions in which the cell expresses the UDP-glycosyltransferase from the polynucleotide.

7. The method of claim 6, further comprising producing steviol-19-O-glycoside by contacting the UDP-glycosyltransferase produced by the recombinant host cell with at least steviol and a nucleotide sugar.

8. The method of claim 7, wherein contacting the UDP-glycosyltransferase produced by the host cell with at least steviol and a nucleotide sugar comprises incubating the recombinant host cell with at least the steviol and the nucleotide sugar, and the method further comprises:
   allowing the UDP-glycosyltransferase to glycosylate steviol at its C-19 position to produce steviol-19-O-glycoside; and
   extracting the steviol-19-O-glycoside from the recombinant host cell.

9. The method of claim 7, wherein the nucleotide sugar is selected from the group consisting of UDP-glucose and UDP-rhamnose.

10. A method for producing a steviol glycoside, the method comprising contacting a composition comprising steviol with a recombinant UDP-glycosyltransferase, the recombinant UDP-glycosyltransferase comprising an amino acid sequence having at least 95% sequence identity to SEQ ID NO: 2 or SEQ ID NO: 4.

11. The method of claim 10, wherein the composition further comprises a nucleotide sugar.

12. The method of claim 10, wherein the nucleotide sugar is selected from the group consisting of UDP-glucose and UDP-rhamnose.

13. The method of claim 10, wherein the recombinant UDP-glycosyltransferase glycosylates steviol at a C-19 position to produce steviol-19-O-glycoside.

14. A recombinant host cell comprising a modified level of a UDP-glycosyltransferase relative to a wild-type cell of the same taxon, wherein the recombinant host cell is capable of producing steviol-19-O-glycoside when the UDP-glycosyltransferase is contacted with steviol and a nucleotide sugar, and wherein the recombinant host cell comprises a polynucleotide selected from:
   a polynucleotide comprising a heterologous regulatory element operably linked to a polynucleotide sequence encoding a polypeptide comprising the amino acid sequence of SEQ ID NO: 2; or a polynucleotide comprising a heterologous regulatory element operably linked to a polynucleotide sequence encoding a polypeptide comprising the amino acid sequence of SEQ ID NO: 4.

15. The recombinant host cell of claim 14, wherein the recombinant host cell is further capable of producing steviol and a nucleotide sugar.

16. The recombinant host cell of claim 15, wherein the recombinant host cell comprises a modified level of at least one of steviol and the nucleotide sugar relative to the wild-type cell of the same taxon.

17. The recombinant host cell of claim 15, wherein the recombinant host cell comprises a modified level of steviol-19-O-glycoside relative to the wild-type cell of the same taxon.

18. A multicellular structure comprising one or more cells according to claim 14.

19. The multicellular structure of claim 18, wherein the multicellular structure comprises plant tissue.

20. The multicellular structure of claim 19, wherein the plant tissue comprises tissue of a whole plant of the species *Stevia rebaudiana*.

\* \* \* \* \*